(12) United States Patent
Kwun et al.

(10) Patent No.: US 9,146,215 B2
(45) Date of Patent: Sep. 29, 2015

(54) APPARATUS AND METHOD FOR INSPECTION OF TUBES IN A BOILER

(71) Applicant: Electric Power Research Institute, Inc., Charlotte, NC (US)

(72) Inventors: Hegeon Kwun, San Antonio, TX (US); Matthew Capps, San Antonio, TX (US); James Crane, San Antonio, TX (US); Stanley M. Walker, Midland, NC (US)

(73) Assignee: Electric Power Research Institute, Inc., Charlotte, NC (US)

( * ) Notice: Subject to any disclaimer, the term of this patent is extended or adjusted under 35 U.S.C. 154(b) by 336 days.

(21) Appl. No.: 13/621,923

(22) Filed: Sep. 18, 2012

(65) Prior Publication Data
US 2013/0081486 A1   Apr. 4, 2013

Related U.S. Application Data

(60) Provisional application No. 61/540,922, filed on Sep. 29, 2011.

(51) Int. Cl.
*G01N 29/24* (2006.01)
*F22B 37/10* (2006.01)
(Continued)

(52) U.S. Cl.
CPC ............ *G01N 29/2412* (2013.01); *F22B 37/00* (2013.01); *F22B 37/10* (2013.01); *F22B 37/38* (2013.01); *G01N 29/22* (2013.01); *G01N 2291/0426* (2013.01); *G01N 2291/2634* (2013.01)

(58) Field of Classification Search
CPC .......... F22B 37/00; F22B 37/10; F22B 37/38; G01N 29/22; G01N 29/2412; G01N 2291/0426; G01N 2291/2412; G01N 2291/2634

USPC ............ 73/592, 628–629, 643, 661; 122/504
See application file for complete search history.

(56) References Cited

U.S. PATENT DOCUMENTS 3,289,468 A * 12/1966 Der Veer et al. ................. 73/637
RE26,537 E * 3/1969 Tompkins ...................... 324/226
(Continued)

FOREIGN PATENT DOCUMENTS

EP    297541 A1 * 1/1989 .............. F22B 37/00
JP  59128448 A  * 7/1984 ...................... 73/592
(Continued)

OTHER PUBLICATIONS

Spline (mechanical), From Wikipedia, the free encyclopedia, entry was last modified on Mar. 28, 2014 at 16:14. 4 pages, downloaded from http://en.wikipedia.org/wiki/Spline_(mechanical) on Oct. 3, 2014.*

(Continued)

*Primary Examiner* — Thomas P Noland
(74) *Attorney, Agent, or Firm* — Trego, Hines & Ladenheim, PLLC

(57) ABSTRACT

An apparatus and method for inspection of tubes in a boiler is disclosed. The apparatus includes a sensor adapted to generate and detect guided-waves and a mechanical device adapted to reach into a tube bundle and clamp the sensor onto an interior tube selected for inspection. The mechanical device includes a housing adapted to contain the sensor and an air cylinder adapted to actuate the housing to allow the housing to clamp onto the interior tube.

4 Claims, 2 Drawing Sheets

(51) Int. Cl.
*F22B 37/38* (2006.01)
*G01N 29/22* (2006.01)
*F22B 37/00* (2006.01)

(56) References Cited

U.S. PATENT DOCUMENTS

| | | | | |
|---|---|---|---|---|
| 3,555,887 | A | * | 1/1971 | Wood .............................. 73/643 |
| 3,561,258 | A | * | 2/1971 | Ashford et al. ................. 73/622 |
| 4,312,230 | A | * | 1/1982 | Bricker et al. .................. 73/638 |
| 4,757,258 | A | * | 7/1988 | Kelly et al. .................... 324/220 |
| 4,893,512 | A | | 1/1990 | Tanimoto et al. |
| 5,456,113 | A | | 10/1995 | Kwun et al. |
| 5,457,994 | A | | 10/1995 | Kwun et al. |
| 5,504,788 | A | | 4/1996 | Brooks et al. |
| 5,549,004 | A | * | 8/1996 | Nugent .......... G01N 2291/2634 |
| 5,581,037 | A | | 12/1996 | Kwun et al. |
| 5,767,766 | A | | 6/1998 | Kwun |
| 5,821,430 | A | | 10/1998 | Kwun et al. |
| 6,164,137 | A | * | 12/2000 | Hancock et al. ................ 73/643 |
| 6,212,944 | B1 | | 4/2001 | Kwun et al. |
| 6,294,911 | B1 | | 9/2001 | Shimazawa et al. |
| 6,396,262 | B2 | | 5/2002 | Light et al. |
| 6,404,189 | B2 | | 6/2002 | Kwun et al. |
| 6,429,650 | B1 | | 8/2002 | Kwun et al. |
| 7,019,520 | B2 | * | 3/2006 | Kwun et al. .................. 324/238 |
| 7,821,258 | B2 | | 10/2010 | Vinogradov |
| 7,913,562 | B2 | | 3/2011 | Kwun et al. |
| 8,301,401 | B2 | * | 10/2012 | Morrison et al. ................ 29/24 |
| 8,521,453 | B1 | * | 8/2013 | Silverman et al. .............. 702/56 |
| 8,907,665 | B2 | * | 12/2014 | Rose et al. ......... G01N 29/2412 |
| 2010/0052670 | A1 | | 3/2010 | Kwun et al. |
| 2014/0278193 | A1 | * | 9/2014 | Breon et al. ................... 702/113 |

FOREIGN PATENT DOCUMENTS

| | | | | |
|---|---|---|---|---|
| JP | 01088006 A | * | 4/1989 | ............. F22B 37/02 |
| WO | WO 3060506 A1 | * | 7/2003 | ............. F22B 37/00 |
| WO | WO 2007011269 A1 | * | 1/2007 | ............. G01N 29/22 |
| WO | WO 2007125308 A2 | * | 11/2007 | ............. G01N 29/22 |
| WO | WO 2011002139 A1 | * | 1/2011 | ..... G01N 2291/2634 |

OTHER PUBLICATIONS

Filipas, Alin, European Search Report for EP Patent Application No. EP2574917, Jan. 21, 2013, Munich.

H. Kwun, S.Y. Kim, and G.M. Light, "The Magnetostrictive Sensor Technology for Long-Range Guided-Wave Testing and Monitoring of Structures", Material Evaluation (2003) 61, pp. 80-84, (15 page reprint).

D.N. Alleyne, B. Pavlakovic, M.J.S. Lowe, and P. Cawley, Rapid Long-Range Inspection of Chemical Plant Pipework Using Guided Waves, Insight (2001) 43, pp. 93-96, and 101, (This copy from Review of Progress in Quantitative Nondestructive Examination, vol. 20, pp. 180-187, ed. by D. O. Thompson et al. (2001).

H. Kwun, S.Y. Kim, H. Matsumoto, and S. Vinogradov, "Detection of Axial Cracks in Tube and Pipe Using Torional Guided Waves," Review of Progress in Quantitative Nondestructive Evaluation, American Institute of Physics, (2008) vol. 27A, pp. 193-199.

* cited by examiner

APPARATUS AND METHOD FOR INSPECTION OF TUBES IN A BOILER

This application claims the benefit of Provisional Application No. 61/489,507 filed on May 24, 2011.

BACKGROUND OF THE INVENTION

The present invention relates to an apparatus and method for inspection of tubes in a boiler. More particularly, the invention relates to an apparatus and method for guided-wave inspection of reheater tubes in a boiler.

To prevent reheater tube failures during plant operation, tubes in the reheater banks need to be inspected. If defects are determined to be large enough to cause failure, the damaged sections need to be replaced during planned outages. In a reheater, there are hundreds of tubes arranged in multiple loops in meandering fashion. Not only are the total length of tubes to inspect miles long, most of the tubes are difficult to access for inspection due to the close packed configuration of the reheater tube banks. Because of the cost and time it would take to inspect them comprehensively, the thermal power generating industries rely primarily on visual inspections and limited inspection of sampled areas on the periphery of the bundles for maintenance decisions. The reliability of a boiler reheater would be improved if the maintenance decisions were made based on more comprehensive tube condition data.

Long-range guided wave technique is a recently introduced inspection method for rapidly surveying a long length of pipe or tube for flaws from a single test position without scanning. Now widely used for examining pipelines in processing plants, this technique provides a 100% volumetric inspection of a long length of pipeline—typically more than 100 ft (30 m) in one direction—for inside and outside surface corrosion/erosion defects and circumferential cracks. In general, guided waves can detect 2% to 3% corrosion metal loss areas and circumferential cracks (here % refers to the circumferential cross-section of a flaw relative to the total pipe wall cross-section) and deep (70% through wall or larger) axial cracks. Accordingly, this technique may be useful as an inspection tool to compile comprehensive information on reheater tubes for maintenance decisions.

BRIEF SUMMARY OF THE INVENTION

These and other shortcomings of the prior art are addressed by the present invention, which provides an apparatus for guided-wave inspection of tubes deep within a reheater tube bank from its accessible side without having to spread tubes to gain access.

According to one aspect of the invention, an apparatus for inspecting a tube includes a sensor adapted to generate and detect guided-waves and a mechanical device adapted to reach into a tube bundle and clamp the sensor onto an interior tube selected for inspection. The mechanical device includes a housing adapted to contain the sensor and an air cylinder adapted to actuate the housing to allow the housing to clamp onto the interior tube.

According to another aspect of the invention, an apparatus for inspecting boiler tubes contained in a boiler tube bundle includes a sensor having first and second guided-wave probes adapted to generate and detect guided-waves and a mechanical device adapted to reach into the boiler tube bundle and clamp the sensor onto an interior tube selected for inspection. The mechanical device includes a housing adapted to contain the sensor, an air cylinder adapted to actuate the housing to allow the housing to clamp onto the interior tube, and a handle connected to the air cylinder for allowing the housing and sensor to reach a selected interior tube for inspection. The housing includes a first housing section adapted to secure the first guided-wave probe therein and a second housing section adapted to secure the second guided-wave probe therein.

According to another aspect of the invention, a method of inspecting tubes contained in a tube bundle includes the steps of providing an apparatus having a sensor and a housing adapted to contain the sensor, extending the apparatus into a tube bundle until a desired tube for inspection is reached, and rotating the apparatus until the sensor is positioned over the tube to be inspected. The method further includes the steps of clamping the housing around the tube to be inspected, thereby clamping the sensor around the tube; transmitting a pulse of guided waves into the tube to be inspected and detecting reflected signals; and acquiring data from the reflected signals and determine the condition of the tube.

BRIEF DESCRIPTION OF THE DRAWINGS

The subject matter that is regarded as the invention may be best understood by reference to the following description taken in conjunction with the accompanying drawing figures in which.

DETAILED DESCRIPTION OF THE INVENTION

Figure 1:
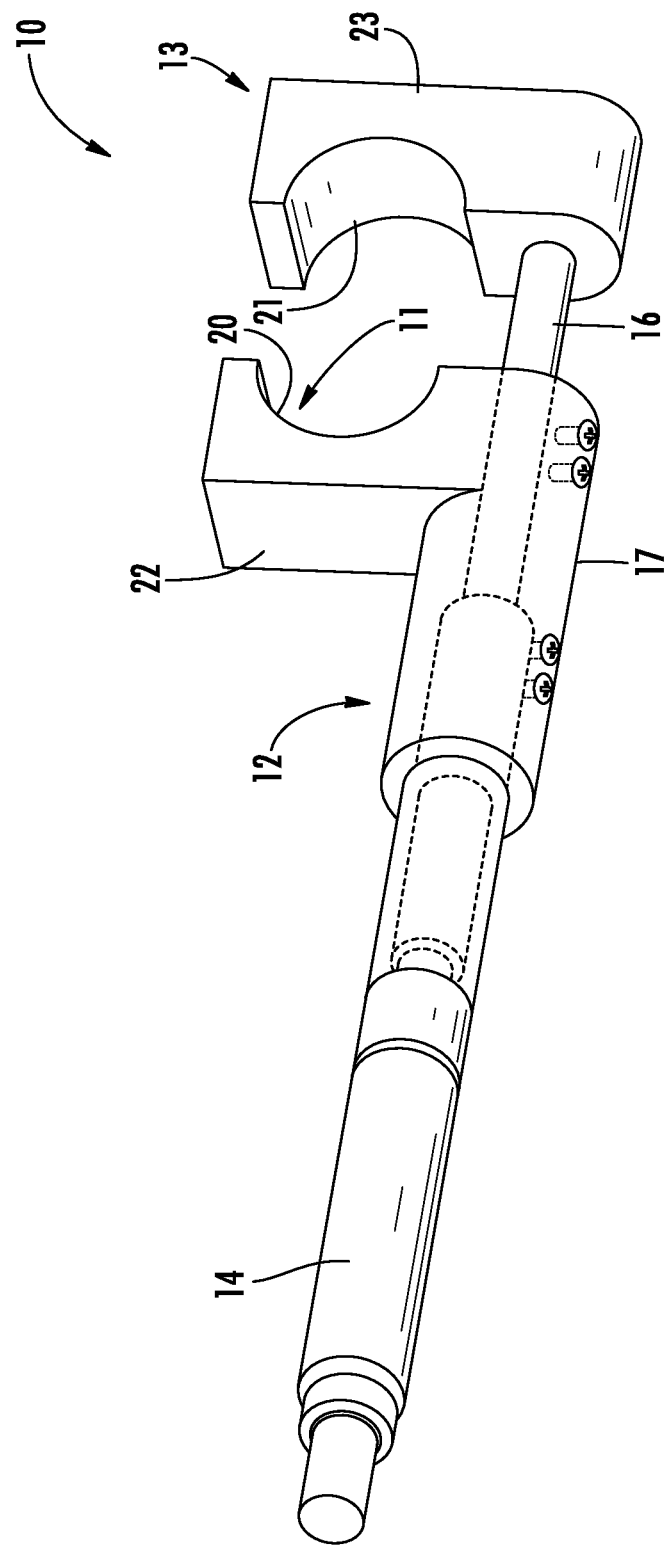
FIG. 1 shows an apparatus according to an embodiment of the invention.

Referring to the drawings, an exemplary apparatus for boiler tube inspection according to an embodiment of the invention is illustrated in FIG. 1 and shown generally at reference numeral 10. The apparatus 10 is composed of two main components. The first component is a sensor 11 that generates and detects guided-waves. The second component is a mechanical device 12 that is capable of reaching into the tube bundle and clamps the sensor 11 onto an interior tube for transmission and reception of guided-waves. As shown, the mechanical device 12 includes a guided wave probe housing 13 for containing the sensor 11 and clamping to the tubes, an air cylinder 14 for actuating the housing 13, a spline 16, and a spline bushing 17. Omitted in the illustration are a long handle, made of cylindrical tube or rod, mechanically fastened to the air cylinder 14 and lead electrical wires to the sensor 11.

The sensor 11 includes two semi-circular guided-wave probes 20 and 21. Each of the probes 20 and 21 are placed and secured in a respective section 22, 23 of the housing 13. The semi-circular guided-wave probes 20 and 21 are made to operate in torsional (T) wave mode based on the methods previously disclosed in U.S. Pat. Nos. 7,821,258 and 7,913,562, both of which utilize magnetostrictive sensor (MsS) technology, and are included herein by reference. It should be appreciated that the apparatus 10 may also be made to operate in other guided-wave modes, such as longitudinal wave mode. However, operating the apparatus 10 in the torsional guided-wave mode is preferred because of dispersion-free characteristics of the torsional mode.

The air cylinder 14 is used to open and close the two probe housing sections 22 and 23. The air cylinder is actuated using pneumatic pressure. The housing 13 is fastened to the spline 16 to assure only linear motion and alignment when the guided-wave apparatus 10 is clamped on a tube with no rotation and bending. The air cylinder 14 is mechanically joined to a long handle 24, FIGS. 2A-2C, for reaching into the tube bundle.

Figure 2C:
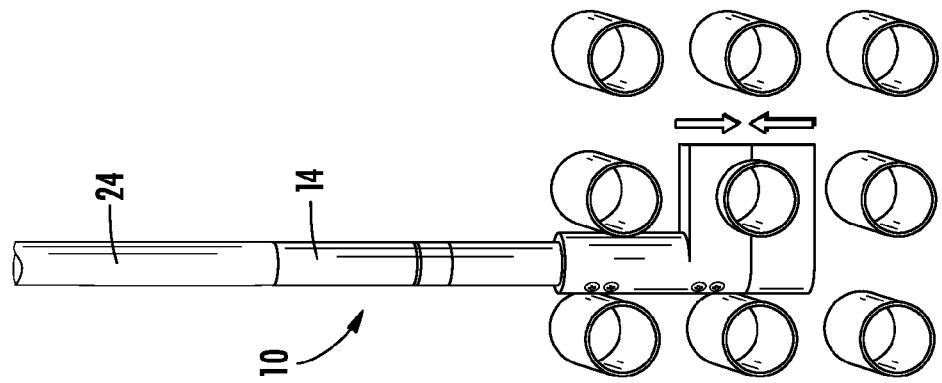
FIGS. 2A-2C illustrate a sequence of testing using the apparatus of FIG. 1.
Figure 2B:
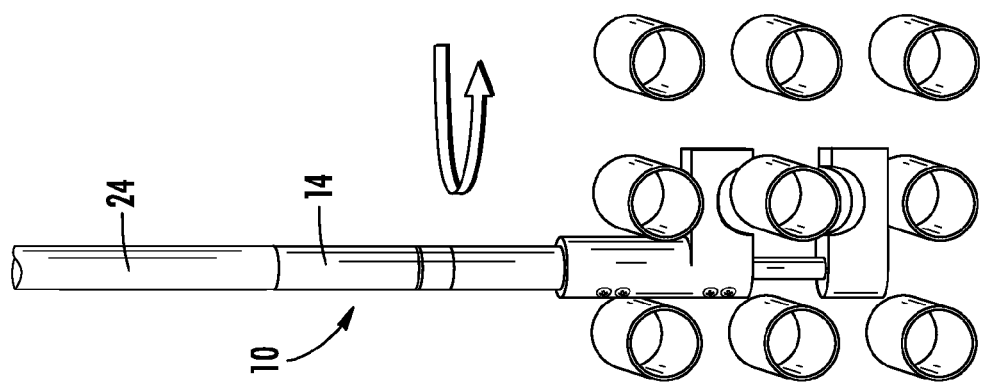
Figure 2A:
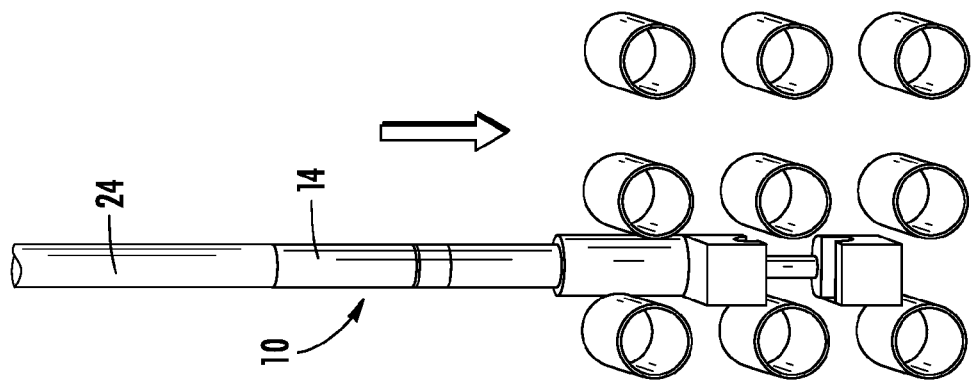

Referring to FIGS. 2A-2C, when inspecting reheater boiler tubes, the apparatus 10 is extended into the bundle to a tube to be tested with the probe housing 13 opened. When the housing 13 part of the apparatus 10 reaches the right depth in the tube bank, the apparatus 10 is rotated by 90° and the semi-circular guided-wave probes 20 and 21 are positioned over the tube. Then the housing 13 is closed to clamp the guided-waves probes 20 and 21 onto the tube. The guided-wave probes 20 and 21 are operated to transmit a pulse of guided waves and detect the signals reflected back in the pulse-echo inspection mode. When data acquisition is completed from the tube, the apparatus 10 is moved to another test location for another measurement.

The minimum clearance required for placement of the apparatus 10 on a tube is approximately 90% of the tube diameter used in the reheater (for example, approximately 1.75 inches for 2-inch OD tubes). Also, while the apparatus 10 is being described in relation to reheater boiler tubes, it should be appreciated that the apparatus may be used in any application that requires inspection of tubes, such as superheater tubes.

The foregoing has described an apparatus and method for inspection of tubes in a boiler. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

We claim:

1. An apparatus for inspecting a tube, comprising:
    a housing comprising two sections, the housing moveable between an open position and a closed position;
    a pair of semi-circular guided-wave probes, wherein each of the guided-wave probes is secured to one of the sections of the housing and arranged such that the guided-wave probes define a cylindrical passage in the closed position; and
    an air cylinder coupled to the housing and configured to move the housing between the open and closed positions along a rectilinear path.

2. The apparatus according to claim 1, further including a spline, wherein the housing is connected to the spline, the spline provides alignment of the housing and allows the housing to only move in a linear direction when the sensor is clamped onto the interior tube.

3. The apparatus according to claim 1, further including a handle connected to the air cylinder.

4. The apparatus according to claim 1, wherein the sensor operates in a torsional (T) wave mode to provide dispersion-free characteristics.

* * * * *